United States Patent [19]

Suzuki et al.

[11] Patent Number: 5,227,037
[45] Date of Patent: Jul. 13, 1993

[54] METHOD AND APPARATUS FOR MEASURING QUANTITY OF ADMIXTURE IN READY-MIXED CONCRETE

[75] Inventors: Kazuo Suzuki, Tokyo; Makoto Takeyama, Urayasu; Hideo Ueda, Minoo; Hisatoshi Sasaki, Kashiwa, all of Japan

[73] Assignees: New Cosmos Electric Co., Ltd.; National Readymixed Concrete Industry Association

[21] Appl. No.: 725,751

[22] Filed: Jun. 20, 1991

[51] Int. Cl.$^5$ .............................. G01N 27/26
[52] U.S. Cl. ..................... 204/153.17; 204/153.13; 204/415
[58] Field of Search ............. 204/153.13, 153.17, 204/415

[56] References Cited

U.S. PATENT DOCUMENTS 3,871,228  5/1973  Weiss ................................ 73/19
4,619,739  10/1986  Kanno et al. .................. 204/153.13
4,741,201  12/1986  Propst ............................... 73/61

FOREIGN PATENT DOCUMENTS 0043229  1/1982  European Pat. Off.
3113785  10/1982  Fed. Rep. of Germany.
3409453  9/1985  Fed. Rep. of Germany.
57-156534  9/1982  Japan.
1-270658  10/1989  Japan.

Primary Examiner—John Niebling
Assistant Examiner—Bruce Bell
Attorney, Agent, or Firm—Jones, Tullar & Cooper

[57] ABSTRACT

A method of measuring the quantity of an admixture in ready-mixed concrete comprises the steps of collecting volatile components generated from the admixture, measuring the concentration of the collected volatile components, and deriving the quantity of the admixture in the ready-mixed concrete from the measured concentration of the volatile components. An apparatus for executing this method comprises a detecting probe and a main measuring unit. The probe includes a gas collecting section and a gas sensor. The main measuring unit for carrying out arithmetic operations on detection information received from the detected probe, and includes a controller for microprocessor the operation of the entire apparatus, and a display for displaying the detected information received from the microprocessor.

11 Claims, 5 Drawing Sheets

METHOD AND APPARATUS FOR MEASURING QUANTITY OF ADMIXTURE IN READY-MIXED CONCRETE

BACKGROUND OF THE INVENTION

1. Field of the Invention

This invention relates to a method of determining the quality of ready-mixed concrete for use in checking, confirming or guaranteeing the quality of the ready-mixed concrete. More particularly, the invention relates to a method and apparatus for measuring the quantity of an admixture in ready-mixed concrete in order to determine the quality of the ready-mixed concrete.

2. Description of the Related Art

Conventionally, the guarantee of quality of ready-mixed concrete of this type is based on slump, the quantity of air mixed into the ready-mixed concrete and the strength of the ready-mixed concrete. These aspects have a great influence on variations in strength following molding and solidification of the concrete and on the durability of the resulting structures. The Japanese Industrial Standard (JIS A5308) requires all three characteristics of ready-mixed concrete to be confirmed in the course of manufacture or shipment of the ready-mixed concrete. Slump is a measure of softness of ready-mixed concrete which is greatly influenced by the quantity of water mixed into the ready-mixed concrete (an air entraining agent, an AE water reducing agent, a high-performance AE water reducing agent and other chemical admixtures for concrete kneaded together at a fixed temperature and mixed with water).

On the other hand, the quantity of an admixture or admixtures mixed into ready-mixed concrete is an important factor greatly influencing the quantity of air and strength.

When ordering ready-mixed concrete, the user of the ready-mixed concrete entrusts the manufacturer with use of admixtures which play an important role in determining the concrete quality as noted above. On the site of operation, the ready-mixed concrete is used after a confirmation is made only of slump and quantity of air.

The quantity of admixtures in ready-mixed concrete has not been confirmed heretofore since the admixture content in the ready-mixed concrete cannot be measured with ease. The user must rely on a report from the manufacturer for the quality of concrete in this respect. Thus, quality control has not been made in the normal routine of operation.

Under the circumstances, the quality of ready-mixed concrete is judged on the site of operation only by appearance and intuition based on experience. For example, admixtures are added in a quantity exceeding a predetermined quantity to the ready-mixed concrete containing low quality aggregate for passing a slump test or the like. In a strength test, the ready-mixed concrete to be used is sampled at the start of use, and compressive strength is measured after molding and curing the test pieces. Therefore, results of the strength measurement are available only upon the lapse of 28 days after the curing.

SUMMARY OF THE INVENTION

An object of the present invention is to eliminate the disadvantages of the prior art noted above and to provide a method and apparatus capable of measuring the quantity of an admixture or admixtures in ready-mixed concrete simply and quickly, thereby to realize a ready-mixed concrete having stability and high quality.

In order to fulfill the above object, a method of measuring the quantity of an admixture in ready-mixed concrete, according to the present invention, comprises the steps of;

collecting volatile components generated from the admixture mixed into the ready-mixed concrete, measuring the concentration of the collected volatile components by using a gas sensor capable of detecting the volatile components, deriving the quantity of the admixture in the ready-mixed concrete from the measured concentration of the volatile components.

An apparatus for measuring a quantity of an admixture in ready-mixed concrete, according to the present invention, comprises a detecting probe dipped into the ready-mixed concrete, and a main measuring unit including a microprocessor for carrying out arithmetic operations on detected information received from the detected probe, and controlling the operation of the entire apparatus, and a display for displaying the detected information received from the microprocessor.

The present invention provides the following functions and effects:

As noted hereinbefore, an admixture is mixed into ready-mixed concrete in order to control the characteristics of the concrete during or after a curing process. This admixture contains volatile components. In the measuring method and apparatus according to the present invention, the volatile components are first collected from the ready-mixed concrete. Then, the concentration of the volatile components is measured with a gas sensor. The concentration of the volatile components generated from the ready-mixed concrete is influenced by the lapse of time and the collecting mode. However, the concentration itself is in an almost perfectly linear relationship to the quantity of admixture mixed into the ready-mixed concrete. This characteristic allows the quantity of admixture mixed into the ready-mixed concrete to be derived from the measured concentration of the volatile components.

According to this method and apparatus, measurement is based on the gaseous concentration of the volatile components generated from the ready-mixed concrete. Thus, measurements may be made at any selected location and instantaneously. Further, this method may be executed by a measuring apparatus having only a gas detecting function and a function to process the detected results. This feature allows the apparatus to be small and lightweight.

It is now possible to measure the quantity of an admixture mixed into ready-mixed concrete or determined the presence or absence of an admixture, as desired, and at any stage, i.e. after preparation of the ready-mixed concrete, immediately after shipment from a plant of the ready-mixed concrete, or on a site of the building operation, for example.

Moreover, the quality of ready-mixed concrete may be determined by measuring the quantity of an admixture. This facilitates the quality control of the ready-mixed concrete, and allows only the ready-mixed concrete containing an admixture or admixtures in a proper quantity to be readily selected for use.

Other features and advantages of the present invention will be apparent from the following description.

DETAILED DESCRIPTION OF THE PREFERRED EMBODIMENTS

A method of measuring the quantity of an admixture in ready-mixed concrete according to the present invention will be described in detail with reference to the drawings.

This admixture measuring method includes a step of collecting volatile components generated from an admixture mixed into ready-mixed concrete; a step of measuring concentration of the collected volatile components by using a gas sensor capable of detecting the volatile components, and a step of deriving the quantity of the admixture in the ready-mixed concrete from the measured concentration of the volatile components.

Figure 1:
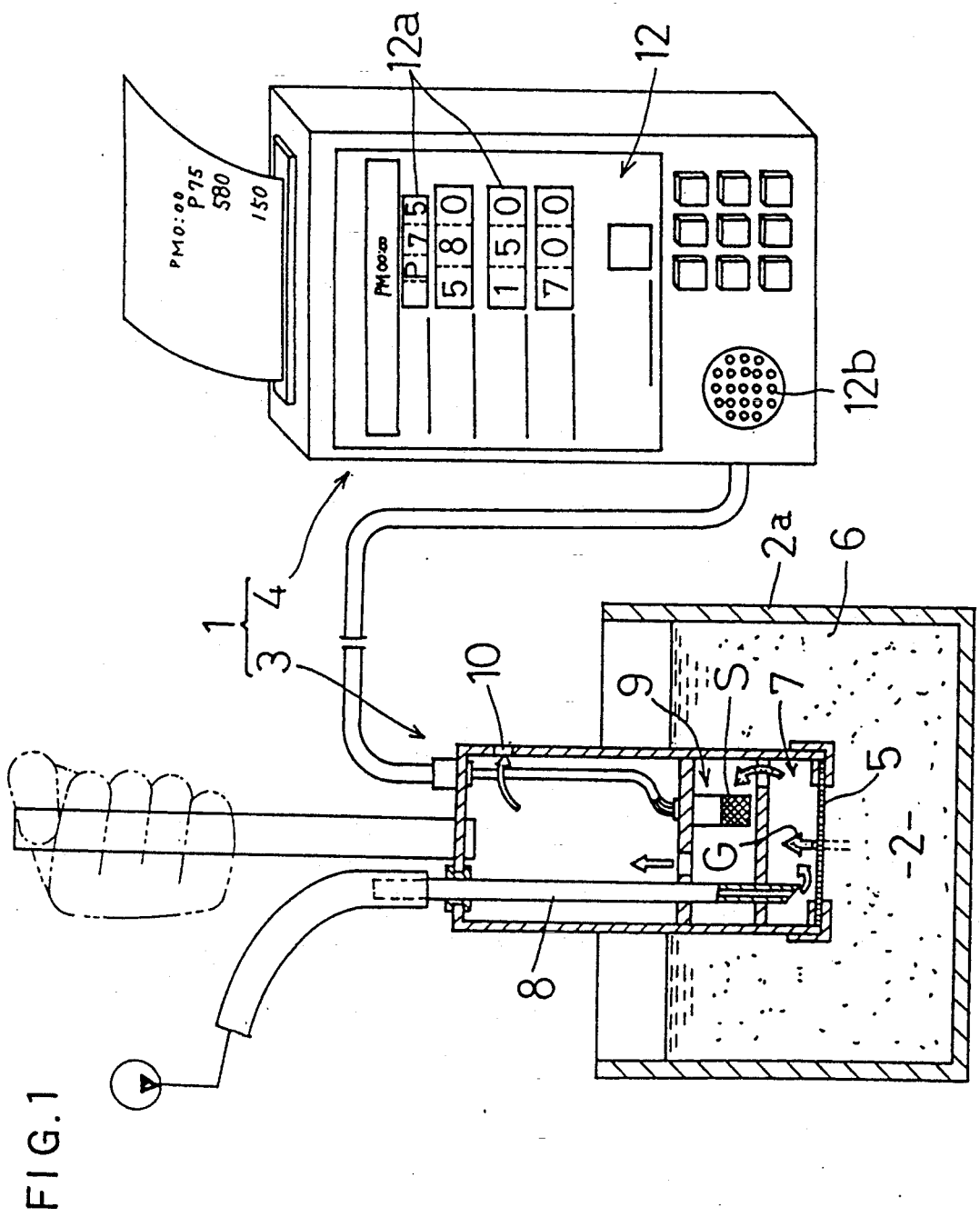
FIG. 1 is a view of an admixture measuring apparatus as used in executing a measuring method according to the present invention.
Figure 2:
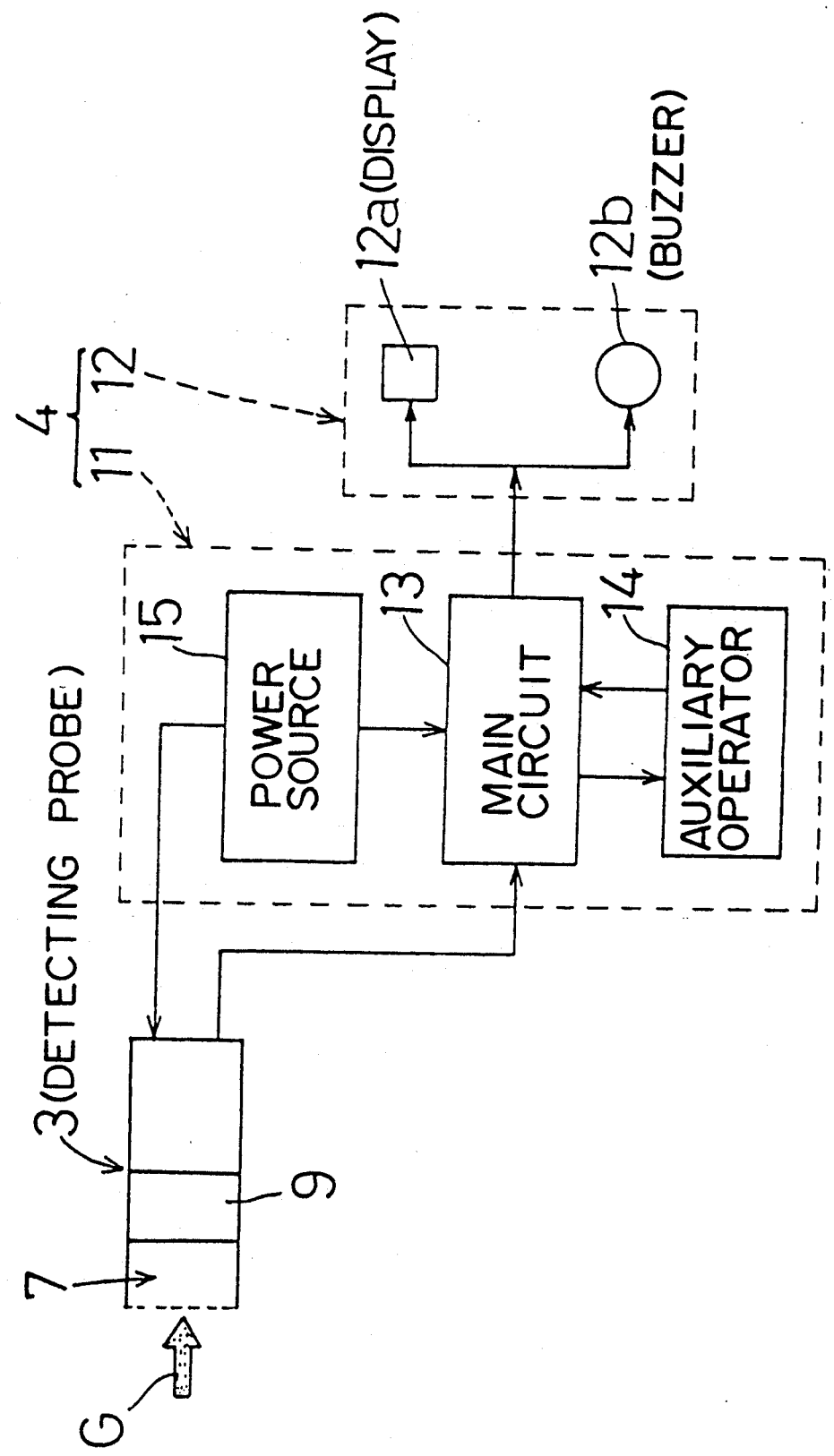
FIG. 2 is a block diagram illustrating the functions of a measuring system.

FIG. 1 shows an admixture measuring apparatus 1 used in executing this method. FIG. 2 is a block diagram showing functions of the measuring apparatus.

The admixture measuring apparatus 1 comprises a detecting probe 3 normally used by being dipped in to the ready-mixed concrete 2, and a main measuring unit 4. The main measuring unit 4 includes a microprocessor 11 for carrying out arithmetic operations on detected information obtained from the detecting probe 3 and controlling an overall operation of the apparatus, and a display 12 for displaying the detected information transmitted from the controller 11.

A mechanism for collecting and measuring volatile components G generated from the admixture 6 in the ready-mixed concrete 2 which is an object of the test will be described first. In using this apparatus, the ready-mixed concrete 2 is placed in a suitable container 2a and the detecting probe 3 is dipped directly into the ready-mixed concrete 2. The detecting probe 3 has a forward end thereof formed of a gas permeable film such as a Teflon film 5. The volatile components G generated from the admixture 6 in the ready-mixed concrete 2 permeate the film 5 to be collected in a gas collecting section 7 defined in the detecting probe 3. The gas collecting section 7 has an air supply tube 8 for supplying fresh ambient air thereto.

The volatile components G of the admixture 6 move upwardly from the gas collecting section 7 entrained with the incoming air through the air supply tube 8. A gas detecting section 9 including a gas sensor S is defined upwardly of the gas collecting section 7 for measuring the gaseous concentration of the volatile components G. After the measurement, the gas is released to the ambient an through an exhaust opening 10 provided in a downstream position with respect to the air flow.

As noted above, the detecting probe 3 includes the gas collecting section 7 for collecting the volatile components G generated from the admixture 6, and the gas detecting section 9 for detecting the concentration of the volatile components G in the gas collecting section 7. The gas detecting section 9 includes the gas sensor S which detects, as a whole or selectively, the concentration of the volatile components G generated from the admixture 6. The gas sensor S may comprise a semiconductor type gas sensor utilizing variations in the electric resistance of a metallic oxide semiconductor occurring through contact with molecules of the volatile components G, a contact combustion type gas sensor or a controlled potential electrolysis type gas sensor. The type and sensitivity of the sensor may be selected to be best suited in view of the type and other aspects of the admixture to be tested.

A signal output from the gas detecting section 9 is processed by the microprocessor 11. The microprocessor 11 includes a main circuit 13 for processing the information received from the gas detecting section 9, and an auxiliary operator 14 for carrying out an arithmetic operation on the information received from the main circuit 13. The main circuit 13 includes a voltage-to-frequency converter and an amplifier for converting variations in the electric resistance or the like of the gas sensor S into a signal and outputting the signal for display, as well as a switching circuit and a sensitivity adjusting circuit to cope with different types of admixture and types of cement and aggregate. The auxiliary operator 14 includes a CPU for calculating compensations for types of the admixture 6, controlling of a gas concentration detecting time and compensations for temperature and humidity. The auxiliary operator 14 is also operable to check whether or not the admixture 6 is contained in a permissible quantity in the ready-mixed concrete 2, to determine the availability of the ready-mixed concrete 2.

The microprocessor 11 further includes a power source 15 for operating the gas sensor S, the main circuit 13 including the auxiliary operator 14, and the display 12 described hereinafter.

The display 12 will be described next. As shown in FIGS. 1 and 2, the display 12 includes a display panel 12a for showing the test date and place, name of the admixture, upper and lower permissible limits of the admixture which are input by a tester, and measurement readings the reflecting readings of the admixture. The display 12a also shows a judgment as to the aptitude value of the admixture 6 in the ready-mixed concrete 2. Further, only the presence or absence of the admixture 6 added to the ready-mixed concrete 2 may be determined and, when the volatile components G exceed a predetermined concentration, this is notified by a buzzer 12b. However, this notifying device is not limited to the buzzer but may be in the form of speech or the lighting of a lamp.

To facilitate maintenance of the measured data, the apparatus has a function to print out the measured data and the like as displayed on the display panel 12a.

Results of admixture measurement using the above admixture measuring apparatus 11 will be described with reference to FIG. 3.

Figure 3:
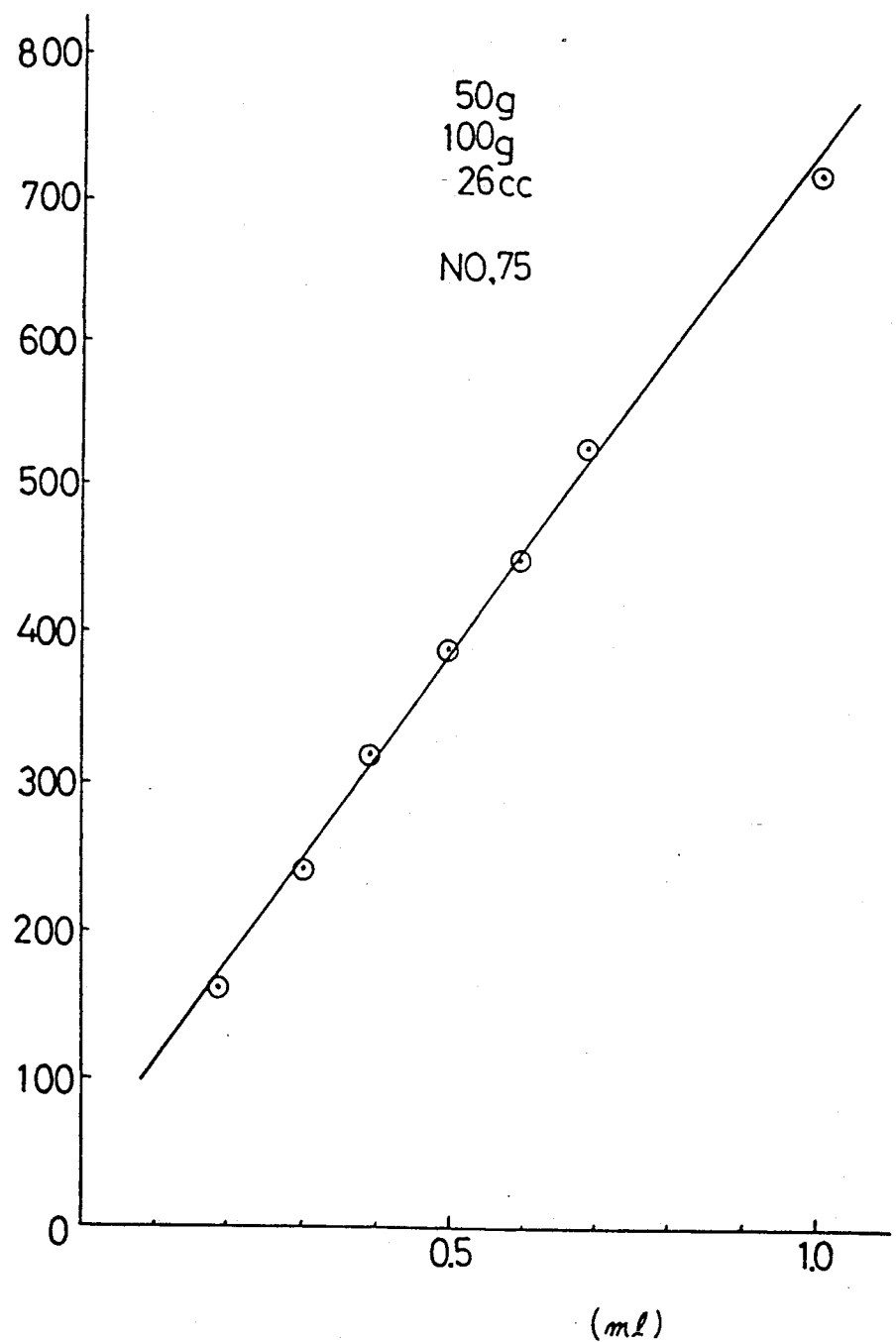
FIG. 3 is a graph showing a relationship between the actual quantities of an admixture and the measured readings in the method of the present invention.

FIG. 3 shows a relationship between the actual quantities of an admixture contained in a ready-mixed concrete (horizontal axis) and readings provided by the measuring apparatus 1 of the present invention (vertical axis). The ready-mixed concrete used in the test was made up of 50 g of ordinary cement (ASTM C150 Type 1), 100 g of sand, and an aggregate of liquid POZ- ZOLITH No. 75 (manufactured by NMB Co., Ltd.) mixed with 26 cc of tap water. In this test, the admixture was added in 0.2, 0.5 and 1.0 ml. Within the scope of this test, the results show that the actual quantities of the admixture and the measured readings are in a perfectly primary linear relationship. The quantity of an admixture or admixtures mixed for use is normally 0.5 ml. With 1.0 ml of an admixture added, concrete would crack. It is thus evident that the above scope of the testing is sufficient for allowing confirmation of the quantity of an admixture to be made by measuring the volatile components G.

Figure 4:
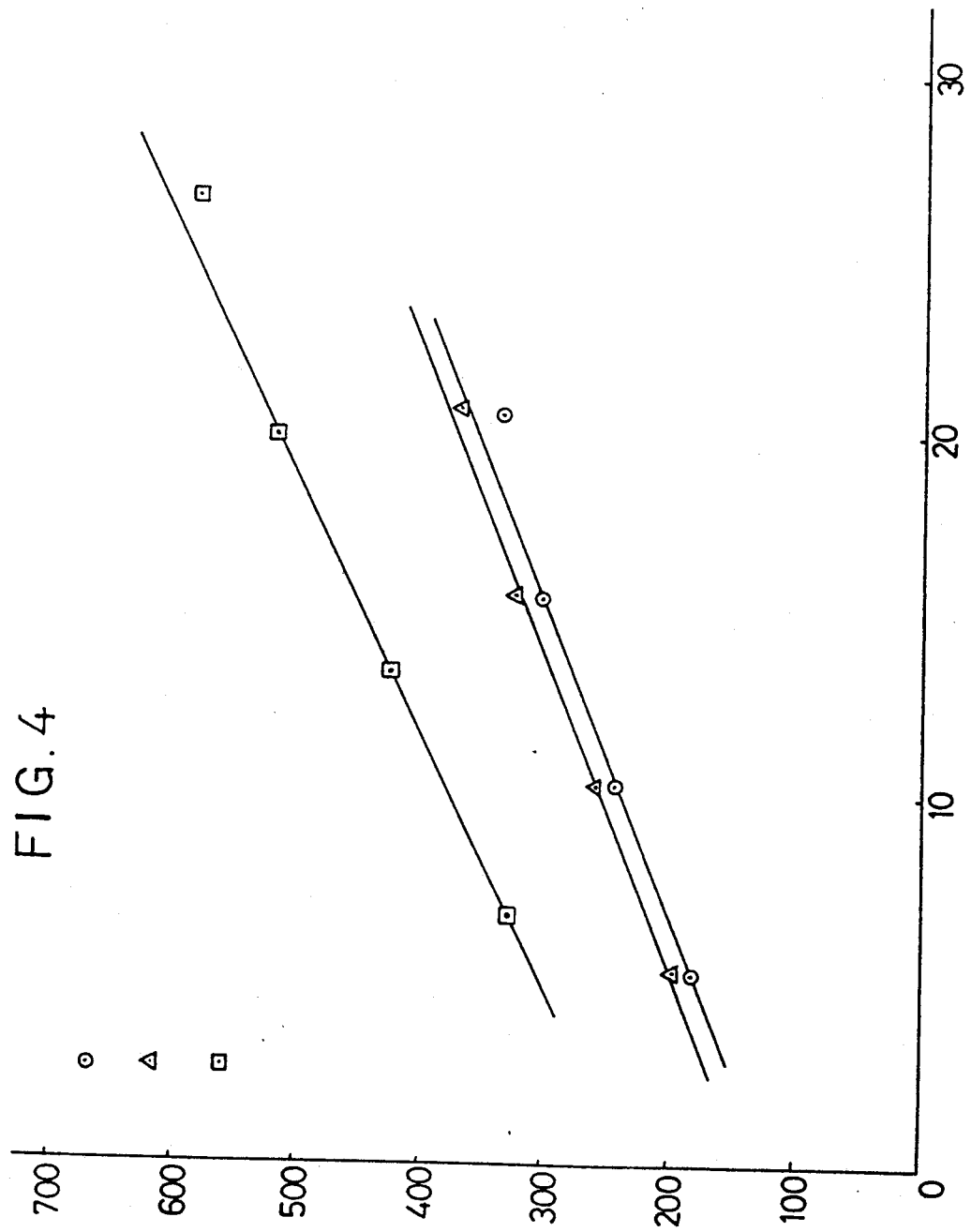
FIG. 4 is a graph showing a relationship between the actual quantities of different admixtures and the measuremed readings, and FIGS. 5 (a) through (f) are views showing detecting probes in different embodiments of the present invention.

FIG. 4 shows the results obtained from the same measuring method executed for admixtures other than the above-mentioned admixture.

The admixtures used in the test were SP-9N (manufactured by NMB Co., Ltd.), MIGHTY (manufactured by Kao Corporation) and SANFLO (manufactured by Sanyo Kokusaku Pulp Co., Ltd.) In this case also, a linear relationship is established between the actual quantities of the admixtures used (horizontal axis) and the measured readings (vertical axis).

Table 1 shows the repeatability of the readings due to differences in the quantity of SP-9N (manufactured by NMB Co., Ltd.) which was used as an admixture to vary the water-cement ratio. In the table, the normal quantity of a high-performance AE water reducing agent added is 1.0, and ½ times the normal quantity is expressed as 0.5 and 3/2 times the normal quantity as 1.5. As seen from the table, excellent repeatability was obtained.

The foregoing results show that this method is capable of measuring the quantity of an admixture in ready-mixed concrete, confirming the quantity of the admixture in the ready-mixed concrete which has a great influence on the quality of the concrete, and confirming the quality of concrete easily and instantaneously.

Further, the type of admixture 6 and the quantity and type of volatile components G based on materials and other conditions of the ready-mixed concrete 2 may be input to the admixture measuring apparatus 1 utilizing this method. Then, a proper quantity of the admixture in the ready-mixed concrete may be determined on a site of operation, for example, by dipping the detecting probe 3 in the ready-mixed concrete.

The detecting probe 3 of the admixture measuring apparatus 1 using the method of the present invention may be modified in various ways. Some modifications will be described hereinafter with reference to FIGS. 5(a) through 5(f).

Figure 5A:
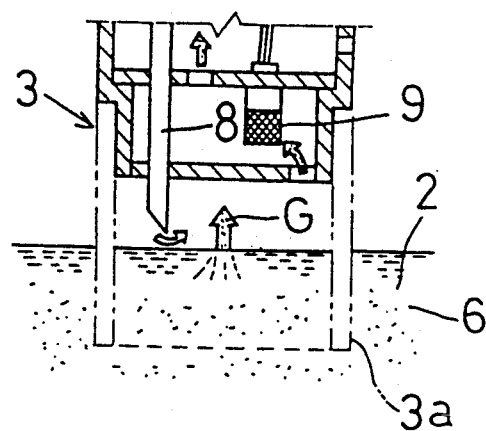

FIG. 5(a) shows a construction similar to the foregoing embodiment, in which a forward portion 3a is replaceable. In this example, the detecting probe 3 is not entirely dipped into the ready-mixed concrete 2 but only part of the forward portion 3a is dipped for use.

Figure 5B:
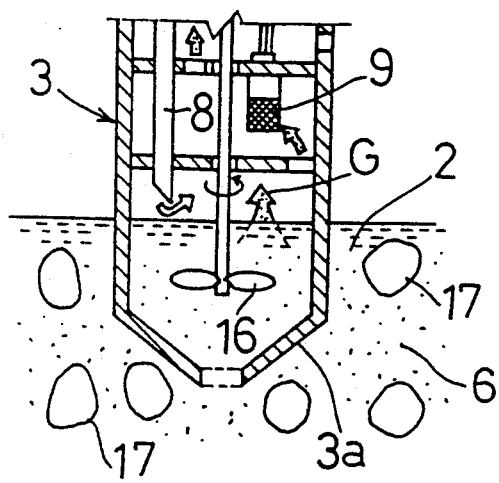

In FIG. 5(b), the detecting probe 3 includes a fan 16 mounted therein for agitating the ready-mixed concrete 2. This detecting probe 3 further includes a conical forward portion 3a for avoiding entry to the detecting probe 3 of solids such as stones 17 in the ready-mixed concrete 2.

Figure 5C:
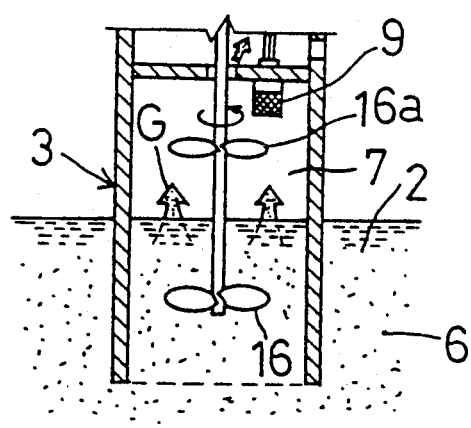

In FIG. 5(c), the gas collecting section 7 also includes an agitating fan 16a instead of the air supply tube 8. Measurement may be carried out while driving the fans 16 and 16a.

Figure 5D:
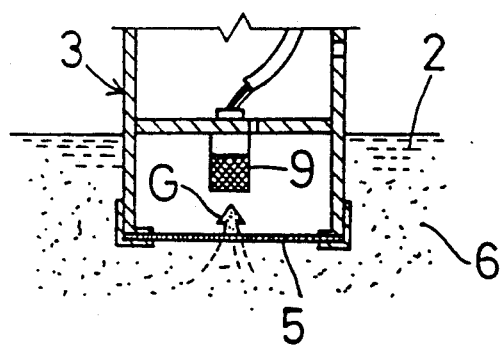
Figure 5E:
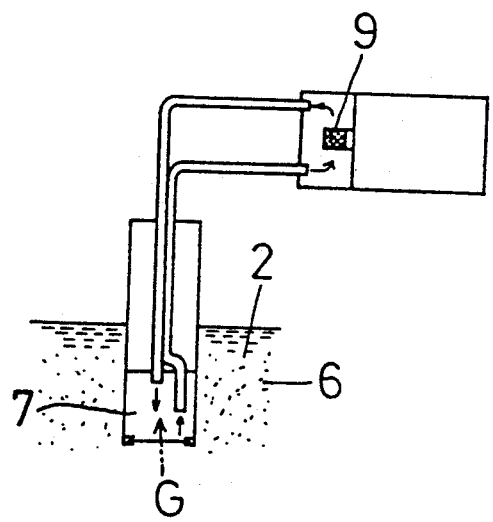
Figure 5F:
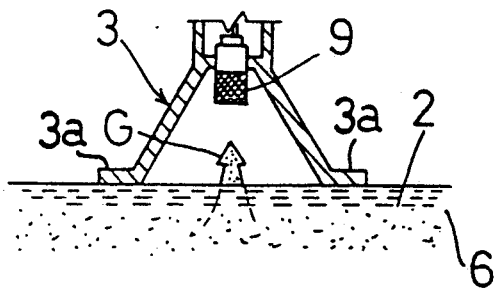

FIG. 5(d) shows a totally closed type detecting probe 3 which shuts off the ready-mixed concrete 2 and which does not use air. This construction is effective where little volatile components are generated.

In FIG. 5 (e), the gas is circulated for detection, with the gas detecting section 9 disposed away from the ready-mixed concrete 2.

In FIG. 5 (f), the detecting probe 3 includes a diverging forward end 3a which contacts a free surface of the ready-mixed concrete 2 for measurement.

Furthermore, the microprocessor 11 in the foregoing embodiment may includes a drive circuit for driving a pump connected to the air supply tube 8 for supplying air to the gas collecting section 7.

The buzzer 12b may be replaced with blinking of a light bulb or a light emitting element or a voice synthesizer to act as an indicator for notifying that the volatile components G have reached a predetermined concentration.

TABLE 1

REFERENCE DATA FOR MEASUREMENT READING
REPEATABILITY OF ADMIXTURE MEASURING APPARATUS

| | WATER-CEMENT RATIO | | | | | | | | |
|---|---|---|---|---|---|---|---|---|---|
| | 0.4 | | | 0.5 | | | 0.6 | | |
| | H.P.AE WATER REDUCING AGENT ADDED | | | | | | | | |
| | 0.5 | 1.0 | 1.5 | 0.5 | 1.0 | 1.5 | 0.5 | 1.0 | 1.5 |
| MEASUREMENT NUMBER | | | | | | | | | |
| 1 | 177 | 201 | 222 | 180 | 240 | 290 | 182 | 215 | 248 |
| 2 | 180 | 200 | 225 | 181 | 238 | 285 | 186 | 221 | 253 |
| 3 | 176 | 195 | 220 | 178 | 237 | 293 | 184 | 218 | 246 |
| 4 | 175 | 203 | 221 | 182 | 235 | 292 | 184 | 218 | 246 |
| 5 | 177 | 198 | 224 | 183 | 236 | 291 | 187 | 217 | 249 |
| 6 | 181 | 200 | 226 | 179 | 238 | 288 | 185 | 219 | 251 |
| 7 | 176 | 202 | 220 | 180 | 239 | 290 | 184 | 216 | 250 |
| 8 | 178 | 198 | 219 | 178 | 235 | 290 | 185 | 216 | 252 |
| 9 | 177 | 197 | 223 | 179 | 235 | 292 | 189 | 215 | 249 |
| 10 | 179 | 196 | 221 | 178 | 236 | 291 | 181 | 215 | 248 |
| AVERAGE VALUE | 177.6 | 199.0 | 222.1 | 179.8 | 236.9 | 290.2 | 184.7 | 217 | 249.2 |
| STANDARD DEVIATION | 1.88 | 2.62 | 2.33 | 1.75 | 1.79 | 2.30 | 2.31 | 2.00 | 2.34 |
| VARIATION COEFFICIENT | 1.06 | 1.32 | 1.05 | 0.97 | 0.76 | 0.79 | 1.25 | 0.92 | 0.94 |

What is claimed is:

1. A method of measuring the quantity of an admixture in a ready-mixed concrete, comprising the steps of:
   collecting a volatile component from the ready-mixed concrete, said volatile component being generated from the admixture mixed into the ready-mixed concrete, by placing a detecting probe having a gas collecting portion and a gas sensor into the ready-mixed concrete;
   measuring the concentration of the collected volatile component using the gas sensor to detect the volatile component; and
   deriving the quantity of the admixture in the ready-mixed concrete from the measured concentration of the volatile component.

2. The method as claimed in claim 1, wherein one of a semiconductor type gas sensor, a contact combustion type gas sensor and a controlled potential electrolysis type gas sensor is used.

3. The method as claimed in claim 2, wherein said gas sensor is mounted in a detecting probe having a replaceable forward element, said gas sensor being used with said forward element removed.

4. The method as claimed in claim 2, wherein said gas sensor is mounted in a detecting probe including a fan for agitating the ready-mixed concrete, measurement being made while agitating the ready-mixed concrete.

5. The method as claimed in claim 4, wherein said detecting probe further includes a fan for agitating a gas collected therein, measurement being made while driving one or both of the fans.

6. The method as claimed in claim 4, wherein said forward element of said detecting probe has a conical shape.

7. The method as claimed in claim 2, wherein said detecting probe is completely sealed.

8. The method as claimed in claim 2, wherein said gas sensor is mounted in a gas detecting section formed separately from a gas collecting section, a gas being circulated for detection.

9. The method as claimed in claim 2, wherein said gas sensor is mounted in a detecting probe having a diverged forward end for contacting a free surface of the ready-mixed concrete, measurement being made while said forward end is contacting the free surface of the ready-mixed concrete.

10. The method as claimed in claim 2, further comprising the step of recording data resulting from the step of deriving quantity of the admixture.

11. A method as claimed in claim 5, wherein said forward element of said detecting probe has a conical shape.

* * * * *